(12) United States Patent
Hwang et al.

(10) Patent No.: US 10,391,233 B2
(45) Date of Patent: Aug. 27, 2019

(54) DRUG DELIVERY KIT, AND APPARATUS AND METHOD FOR PREPARING DRUG DELIVERY SYSTEM

(71) Applicant: TGEL BIO CO., LTD., Seoul (KR)

(72) Inventors: Changsoon Hwang, Incheon (KR); Sun Jong Kim, Seoul (KR); Han Weon Cho, Seoul (KR); Sunhee Ham, Gangwon-do (KR); Hyesook Chung, Seoul (KR)

(73) Assignee: TGEL BIO CO., LTD., Seoul (KR)

( * ) Notice: Subject to any disclaimer, the term of this patent is extended or adjusted under 35 U.S.C. 154(b) by 118 days.

(21) Appl. No.: 15/509,161

(22) PCT Filed: Apr. 19, 2016

(86) PCT No.: PCT/KR2016/004072
§ 371 (c)(1),
(2) Date: Mar. 6, 2017

(87) PCT Pub. No.: WO2016/171450
PCT Pub. Date: Oct. 27, 2016

(65) Prior Publication Data
US 2017/0274137 A1    Sep. 28, 2017

(30) Foreign Application Priority Data

Apr. 20, 2015 (KR) .................. 10-2015-0055410

(51) Int. Cl.
*A61M 5/00* (2006.01)
*A61M 5/32* (2006.01)
(Continued)

(52) U.S. Cl.
CPC .............. *A61M 5/002* (2013.01); *A61M 5/32* (2013.01); *A61J 1/1412* (2013.01); *A61M 5/178* (2013.01); *A61M 2205/3368* (2013.01)

(58) Field of Classification Search
CPC .......... A61J 1/1412; A61M 2205/3368; A61M 5/002; A61M 5/178; A61M 5/32
See application file for complete search history.

(56) References Cited

U.S. PATENT DOCUMENTS 4,865,986 A * 9/1989 Coy .................... B01L 7/52
435/285.1
5,040,678 A * 8/1991 Lenmark, Sr. ....... B65D 81/107
206/204

(Continued)

FOREIGN PATENT DOCUMENTS

JP    2001-286561 A    10/2001
JP    2005-262013 A    9/2005
(Continued)

*Primary Examiner* — Tony G Soohoo
(74) *Attorney, Agent, or Firm* — Novick, Kim & Lee, PLLC; Jae Youn Kim

(57) ABSTRACT

Disclosed is a drug delivery kit, including an apparatus for preparing a drug delivery system, which includes therein a drug carrier in a gel phase or a solid phase under the airtight condition, and has therein a mixing space configured such that a drug for forming a drug delivery system with the drug carrier is injected from the outside and is mixed with the drug carrier, and a syringe for injecting the drug into the apparatus for preparing a drug delivery system. Also, an apparatus for preparing a drug delivery system, which can be applied to the drug delivery kit, and a method of preparing a drug delivery system using the apparatus are provided. The drug delivery system can be easily prepared on site, whereby the drug can be delivered in vivo.

23 Claims, 15 Drawing Sheets

(51) Int. Cl.
*A61M 5/178* (2006.01)
*A61J 1/14* (2006.01)

(56) References Cited

U.S. PATENT DOCUMENTS

| | | | | |
|---|---|---|---|---|
| 5,044,428 | A * | 9/1991 | Nohl | B01F 11/0028 165/109.1 |
| 5,614,089 | A * | 3/1997 | Allington | B01D 11/0203 210/198.2 |
| 5,773,024 | A * | 6/1998 | Unger | A61K 8/046 424/450 |
| 6,123,688 | A * | 9/2000 | Botich | A61M 5/24 604/110 |
| 6,146,895 | A * | 11/2000 | Green | G01N 1/2226 366/108 |
| 2002/0118595 | A1* | 8/2002 | Miller | A61L 24/06 366/130 |
| 2004/0024354 | A1* | 2/2004 | Reynolds | A61F 13/0203 604/87 |
| 2007/0079894 | A1* | 4/2007 | Kraus | A61J 1/10 141/319 |
| 2008/0093357 | A1* | 4/2008 | Norman | A47J 36/2433 219/521 |
| 2011/0106045 | A1* | 5/2011 | Reynolds | A61J 1/2096 604/413 |
| 2013/0237904 | A1 | 9/2013 | Deneburg et al. | |
| 2014/0078854 | A1* | 3/2014 | Head | A61M 5/002 366/111 |
| 2014/0295435 | A1* | 10/2014 | Su | C12Q 1/689 435/6.12 |
| 2016/0008777 | A1* | 1/2016 | Patel | B01F 11/0005 424/94.67 |
| 2016/0008779 | A1* | 1/2016 | Seaward | B01F 11/0054 366/273 |
| 2016/0206511 | A1* | 7/2016 | Garfield | A61J 1/2089 |
| 2018/0045627 | A1* | 2/2018 | Blankenstein | G01N 35/1002 |

FOREIGN PATENT DOCUMENTS

| | | |
|---|---|---|
| JP | 2006-500190 A | 1/2006 |
| JP | 2007-260162 A | 10/2007 |
| JP | 2008-517927 A | 5/2008 |
| JP | 2009-268466 A | 11/2009 |
| JP | 2010-525863 A | 7/2010 |
| JP | 2011-72440 A | 4/2011 |
| JP | 2012-140425 A | 7/2012 |
| JP | 2013-543756 A | 12/2013 |
| JP | 2015-002752 A | 1/2015 |
| KR | 10-2007-0100701 A | 10/2007 |
| KR | 10-1072389 B1 | 10/2011 |
| KR | 10-2012-0013962 A | 2/2012 |
| WO | 95/03036 A1 | 2/1995 |
| WO | 00/00222 A1 | 1/2000 |
| WO | 2006/015117 A1 | 2/2006 |
| WO | 2010/128394 A2 | 11/2010 |
| WO | 2015-002011 A1 | 1/2015 |

\* cited by examiner

DRUG DELIVERY KIT, AND APPARATUS AND METHOD FOR PREPARING DRUG DELIVERY SYSTEM

TECHNICAL FIELD

The present invention relates to a drug delivery kit and an apparatus and method for a drug delivery system and, more particularly, to a drug delivery kit, which facilitates the on-site preparation of a drug delivery system so as to deliver a drug in vivo, an apparatus for preparing a drug delivery system, which may be applied to the drug delivery kit, and a method of preparing a drug delivery system using the apparatus.

BACKGROUND ART

A drug delivery system, useful for delivering a drug in vivo, is made up of a drug and a drug carrier. Such a drug delivery system is typically manufactured in the state of a drug being loaded, but sufficient effort to develop techniques for on-site preparation of a drug delivery system has not been made.

CITATION LIST

Patent Literature (Patent Document 1) Korean Patent No. 10-1072389, Oct. 11, 2011, Claims

DISCLOSURE OF INVENTION

Technical Problem

Accordingly, the present invention has been made keeping in mind the above problems occurring in the related art, and the present invention is intended to provide a drug delivery kit, which facilitates the on-site preparation of a drug delivery system to deliver a drug in vivo.

In addition, the present invention is intended to provide an apparatus for preparing a drug delivery system, which may be applied to the drug delivery kit.

In addition, the present invention is intended to provide a method of preparing a drug delivery system using the apparatus.

Additional technical problems, which are not mentioned in the foregoing, will be readily understood by those skilled in the art from the following description.

Solution to Problem

The present invention provides a drug delivery kit, comprising: an apparatus for preparing a drug delivery system, which includes therein a drug carrier in a gel phase or a solid phase under the airtight condition, and has therein a mixing space configured such that a drug for forming a drug delivery system with the drug carrier is injected from the outside and is mixed with the drug carrier; and a syringe for injecting the drug into the apparatus for preparing a drug delivery system.

The drug may be injected into the apparatus for preparing a drug delivery system, together with or separately from a solvent.

The solvent may be a solvent for forming the drug delivery system.

The drug may be dissolved or suspended in a solvent, or at least a portion of the drug may be contained in a microsphere. Preferably, the drug is dissolved or suspended in a solvent, or a portion of the drug is contained in a microsphere.

The drug, which is dissolved or suspended in the solvent, may be at least a portion of the drug, and is preferably all of the drug.

The solvent may be a solvent for dissolving or suspending the drug carrier.

At least one solvent, selected from among a solvent for dissolving or suspending the drug carrier and a solvent for dissolving or suspending the drug, may be injected from the outside into the apparatus for preparing a drug delivery system.

The solvent may be water.

The water may be physiological saline.

The water may be deionized water.

The microsphere may be in the state of being suspended in a solvent.

The microsphere may contain at least a portion of the drug, and the remainder of the drug may be dissolved or suspended in the solvent in which the microsphere is suspended.

The drug carrier may include a gel-forming polymer.

The drug carrier may further include a gel-forming assistant for aiding the formation of a polymer gel.

The gel may be a temperature-sensitive hydrogel.

The temperature-sensitive hydrogel may be a liquid at room temperature and may be a solid or gel at body temperature.

The drug delivery system may be a liquid at room temperature and may be a gel or solid at body temperature.

In an exemplary embodiment, the drug delivery system may be a liquid at room temperature and may be a gel or solid at body temperature, owing to dissolution or suspension of the drug carrier in the solvent.

The drug carrier in a solid phase may be a mixture comprising poly(ethylene oxide-propylene oxide-ethylene oxide) and sodium hyaluronate, which are a solid.

The apparatus may include a drug injection part at one side thereof so that a syringe needle is placed in or withdrawn from the apparatus and so that the inside of the apparatus is kept airtight when the syringe needle is placed in or withdrawn from the apparatus.

The drug injection part may include a sealing stopper.

The mixing space may be positioned between the drug injection part and the drug carrier.

The syringe may include a syringe body and a syringe needle.

The apparatus may further include therein a stirring element.

The stirring element may include at least one selected from among a stirring magnet, a stirring rod, a stirring plate, and a stirring ball.

The stirring rod may be provided in the form of a rod, and may include a stirring magnet therein.

At least one side of the stirring rod may include a projection part.

The projection part may be formed in the long-axis direction of the stirring rod.

A portion of the surface of the projection part may be formed to be curvilinear.

The kit may further comprise a temperature control chamber.

The temperature control chamber may include a casing, an apparatus fixer for fixing the apparatus in the casing, and a temperature control medium holding recess for receiving a temperature control medium in the casing.

The casing may include a casing body and a lid.

The casing may include a heat insulation layer formed on at least a portion thereof.

The apparatus fixer may include a first subunit that directly contacts the apparatus and a second subunit for fixedly connecting the first subunit to the casing.

One side of the first subunit may include a fixing end formed to protrude in a direction toward the apparatus so as to fix the apparatus, and the remaining side of the first subunit may be removably fixed to one side of the second subunit.

The inner side of the second subunit may be connected to the outer side of the first subunit, and the outer side of the second subunit may be connected to the inner side of the casing by means of a connector.

The kit may further comprise a stirrer for mixing the drug carrier and the drug, which are maintained in the apparatus for preparing a drug delivery system.

The stirrer may include at least one selected from among a direct stirrer for directly mixing the drug carrier and the drug, an indirect stirrer for indirectly mixing the drug carrier and the drug through motion of the apparatus, and a direct-indirect stirrer for indirectly mixing the drug carrier and the drug while directly mixing the drug carrier and the drug.

The direct stirrer may be a magnetic stirrer or an ultrasonic stirrer.

The indirect stirrer may include at least one selected from among a revolution-rotation stirrer, a vibration stirrer, a rotary stirrer, a vortex mixer, a rotator, a microplate mixer, a shaker, and a roller stirrer.

The direct-indirect stirrer may be a ball mill stirrer.

The magnetic stirrer may include a support for supporting the apparatus for preparing a drug delivery system, and the support may include a holding recess that receives at least a portion of the apparatus for preparing a drug delivery system.

The stirrer may be provided with a temperature controller.

The kit may further comprise a user's guide.

The drug carrier in a solid phase may be a lyophilized material.

In addition, the present invention provides an apparatus for preparing a drug delivery system, which includes therein a drug carrier in a gel phase or a solid phase under the airtight condition, and has therein a mixing space configured such that a drug for forming a drug delivery system with the drug carrier is injected from the outside and is mixed with the drug carrier.

The drug may be injected into the apparatus for preparing a drug delivery system, together with or separately from a solvent.

The solvent may be a solvent for forming the drug delivery system.

The drug may be dissolved or suspended in a solvent, or at least a portion of the drug may be contained in a microsphere. Preferably, the drug is dissolved or suspended in a solvent, or a portion of the drug is contained in a microsphere.

The drug, which is dissolved or suspended in the solvent, may be at least a portion of the drug, and is preferably all of the drug.

The solvent may be a solvent for dissolving or suspending the drug carrier.

At least one solvent, selected from among a solvent for dissolving or suspending the drug carrier and a solvent for dissolving or suspending the drug, may be injected from the outside into the apparatus for preparing a drug delivery system.

The solvent may be water.

The water may be physiological saline.

The water may be deionized water.

The microsphere may be in the state of being suspended in a solvent.

The microsphere may contain a portion of the drug, and the remainder of the drug may be dissolved or suspended in the solvent in which the microsphere is suspended.

The drug carrier may include a gel-forming polymer.

The drug carrier may further include a gel-forming assistant for aiding the formation of a polymer gel.

The gel may be a temperature-sensitive hydrogel.

The temperature-sensitive hydrogel may be a liquid at room temperature and may be a solid or gel at body temperature.

The drug delivery system may be a liquid at room temperature and may be a gel or solid at body temperature.

The drug carrier in a solid phase may be a mixture comprising poly(ethylene oxide-propylene oxide-ethylene oxide) and sodium hyaluronate, which are a solid.

The apparatus may include a drug injection part at one side thereof so that a syringe needle is placed in or withdrawn from the apparatus and so that the inside of the apparatus is kept airtight when the syringe needle is placed in or withdrawn from the apparatus.

The drug injection part may include a sealing stopper.

The mixing space may be positioned between the drug injection part and the drug carrier.

The apparatus may further include therein a stirring element.

The stirring element may include at least one selected from among a stirring magnet, a stirring rod, a stirring plate, and a stirring ball.

The stirring rod may be provided in the form of a rod, and may include a stirring magnet therein.

At least one side of the stirring rod may include a projection part.

The projection part may be formed in the long-axis direction of the stirring rod.

A portion of the surface of the projection part may be formed to be curvilinear.

The apparatus for preparing a drug delivery system may be placed into a temperature control chamber.

The temperature control chamber may include a casing, an apparatus fixer for fixing the apparatus in the casing, and a temperature control medium holding recess for receiving a temperature control medium in the casing.

The casing may include a casing body and a lid.

The casing may include a heat insulation layer formed on at least a portion thereof.

The apparatus fixer may include a first subunit that directly contacts the apparatus and a second subunit for fixedly connecting the first subunit to the casing.

One side of the first subunit may include a fixing end formed to protrude in a direction toward the apparatus so as to fix the apparatus, and the remaining side of the first subunit may be removably fixed to one side of the second subunit.

The inner side of the second subunit may be connected to the outer side of the first subunit, and the outer side of the second subunit may be connected to the inner side of the casing by means of a connector.

The drug carrier in a solid phase may be a lyophilized material.

In addition, the present invention provides a method of preparing a drug delivery system, comprising: (A) providing an apparatus for preparing a drug delivery system, which includes therein a drug carrier in a gel phase or a solid phase under the airtight condition, and has therein a mixing space configured such that a drug for forming a drug delivery system with the drug carrier is injected from the outside and is mixed with the drug carrier; (B) injecting the drug into the apparatus for preparing a drug delivery system; and (C) mixing the drug and the drug carrier in the mixing space, thus forming the drug delivery system.

The drug may be injected into the apparatus for preparing a drug delivery system, together with or separately from a solvent.

The solvent may be a solvent for forming the drug delivery system.

The drug may be dissolved or suspended in a solvent.

The solvent may be a solvent for dissolving or suspending the drug carrier.

Also, the method may further comprise injecting at least one solvent, selected from among a solvent for dissolving or suspending the drug carrier and a solvent for dissolving or suspending the drug, from the outside into the apparatus for preparing a drug delivery system. Here, this injection step may be implemented between the step (A) and the step (B), simultaneously with the step (B), between the step (B) and the step (C), or simultaneously with the step (C).

The solvent may be water.

The water may be physiological saline.

The water may be deionized water.

The apparatus for preparing a drug delivery system may fall under the same scope as the apparatus of the present invention.

The drug may fall under the same scope as the drug injected into the apparatus of the present invention.

The drug carrier may fall under the same scope as the drug carrier contained in the apparatus of the present invention.

The injection step may be performed using a syringe.

The syringe may fall under the same scope as the syringe included in the kit of the present invention.

The mixing step may be performed under the condition that the apparatus, into which the drug and the drug carrier are injected, is placed into a temperature control chamber.

The temperature control chamber may fall under the same scope as the temperature control chamber that may be included in the kit of the present invention.

The mixing step may be performed using a stirring element, which may fall under the same scope as the stirring element that may be included in the apparatus of the present invention.

The mixing step may be performed using a stirrer, which may fall under the same scope as the stirrer that may be included in the kit of the present invention.

Advantageous Effects of Invention

According to the present invention, a drug delivery system can be easily prepared on site so as to deliver a drug in vivo.

DESCRIPTION FOR KEY ELEMENTS IN THE DRAWINGS

Figure 1:
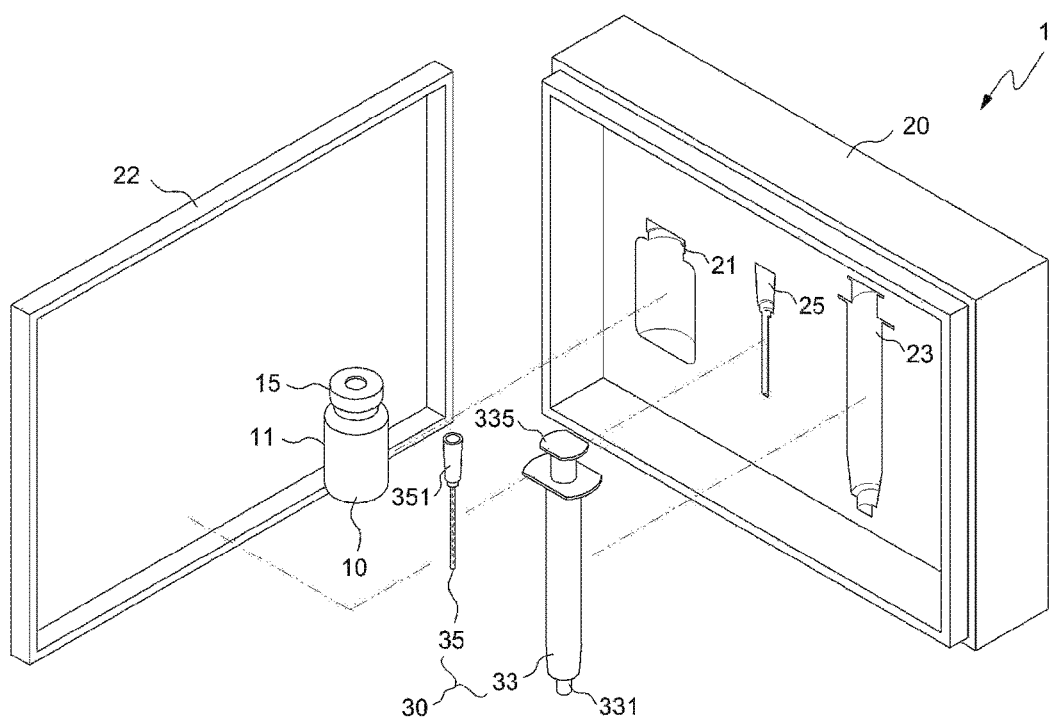
FIG. 1 illustrates a drug delivery kit according to an embodiment of the present invention.

1: drug delivery kit
10, 10-1, 10-2: apparatus for preparing a drug delivery system
11: apparatus body
12: protrusion
13: drug injection part
15: cap
16: opening
17: drug carrier
18, 18-1, 18-2: stirring element
19: mixing space
20: packaging case
21: apparatus holding recess
22: cover
23: syringe body holding recess
25: syringe needle holding recess
30: syringe
33: syringe body
35: syringe needle
50, 50-1, 50-2: stirrer
51: holding recess
52: roller
53: support
55: speed control part
57: temperature controller
59: stirrer body
70: temperature control chamber
71: lid
72: casing
73: casing body
74: fixing ends
75: first subunit
76: apparatus fixer
77: second subunit
78: insertion part
79: connector
183: stirring rod body
185, 187: projection parts
189: stirring magnet
331: syringe needle connector
335: piston
351: body connector
710: coupling part
711, 731: heat insulation layers
713: packing
715: outer coupling part
717: inner coupling part
733: temperature control medium holding recess 739: insertion depression
741: projection

MODE FOR THE INVENTION

Hereinafter, the advantages and features of the present invention will be more clearly understood from the following detailed description taken in conjunction with the accompanying drawings. However, the present invention is not limited to the embodiments disclosed herein, but may be modified into different forms. These embodiments are provided to thoroughly explain the disclosure and to sufficiently transfer the spirit of the present invention to those skilled in the art, and the present invention is merely defined by the scope of the claims.

Throughout the specification, the same reference numerals designate the same components. Also, the term "and/or" may include any one of the limited components and any combination of one or more thereof.

The terminology used herein is for the purpose of describing particular embodiments only and is not intended to limit the invention. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, do not preclude the presence or addition of one or more other components.

As used herein, the term "drug delivery system" refers to a system in the form of a drug carrier containing a drug, comprising a drug and a drug carrier for delivering a drug in vivo.

As used herein, the term "apparatus for preparing a drug delivery system" refers to an apparatus used to prepare a drug delivery system.

As used herein, the term "kit" refers to a group of physically separate components, which may be packaged on a unit basis and may be called a set, a package, etc.

As used herein, the term "drug delivery kit" refers to a unit pack, including apparatuses, devices, and/or parts, suitable for use in delivering a drug in vivo, such as an apparatus for preparing a drug delivery system.

Below is a description of a drug delivery kit, an apparatus for preparing a drug delivery system, and a method of preparing a drug delivery system, according to embodiments of the present invention, with reference to FIGS. 1 to 16.

Figure 2:
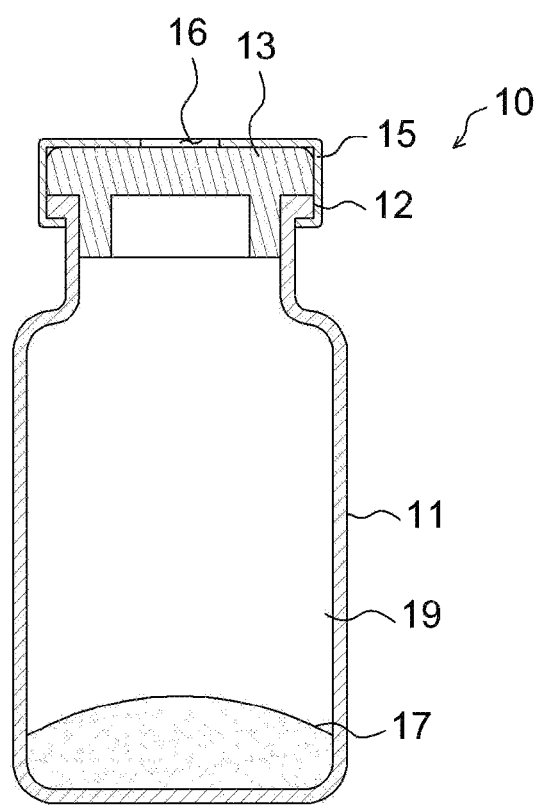
FIG. 2 is a cross-sectional view illustrating an apparatus for preparing a drug delivery system according to an embodiment of the present invention.
Figure 3:
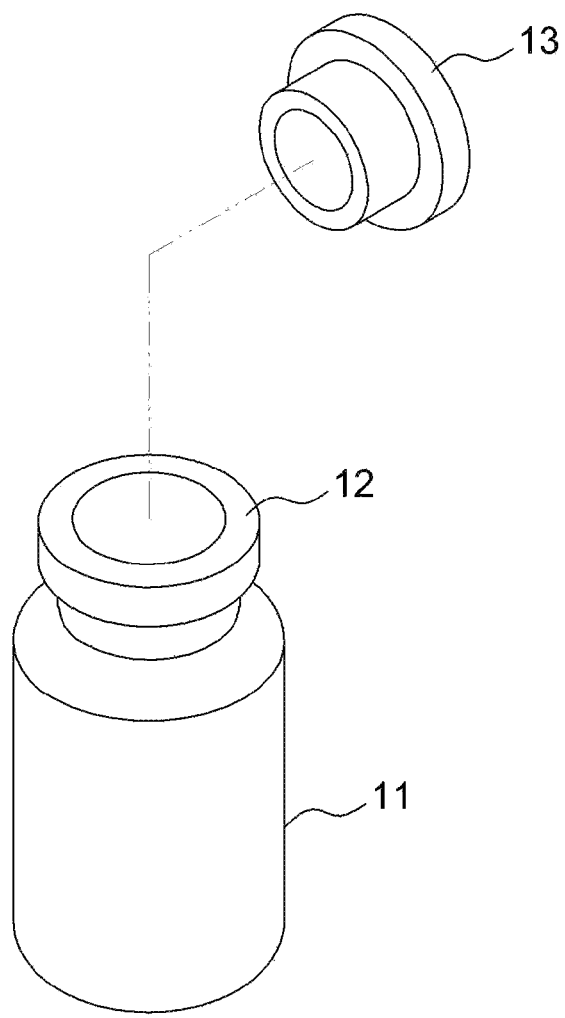
FIG. 3 illustrates a drug injection part and a body of the apparatus of FIG. 2.
Figure 4:
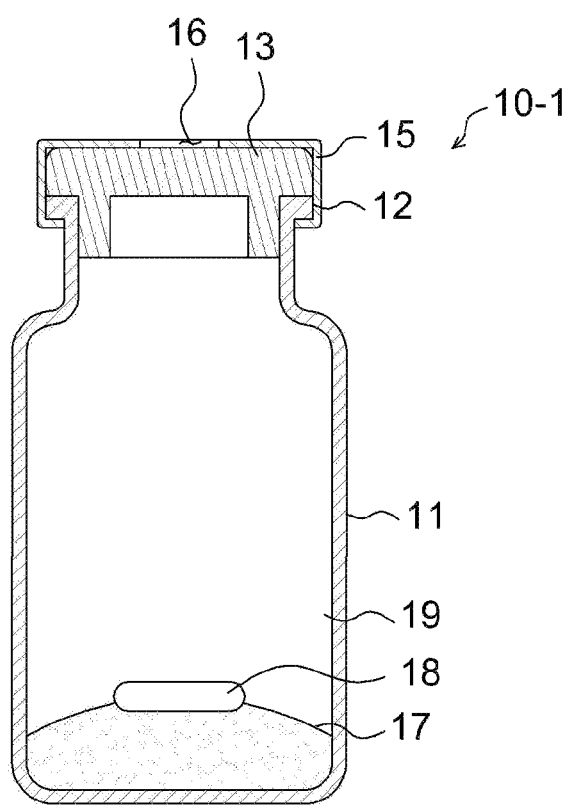
FIG. 4 is a cross-sectional view illustrating an apparatus for preparing a drug delivery system according to a modification of the embodiment of the present invention.
Figure 5:
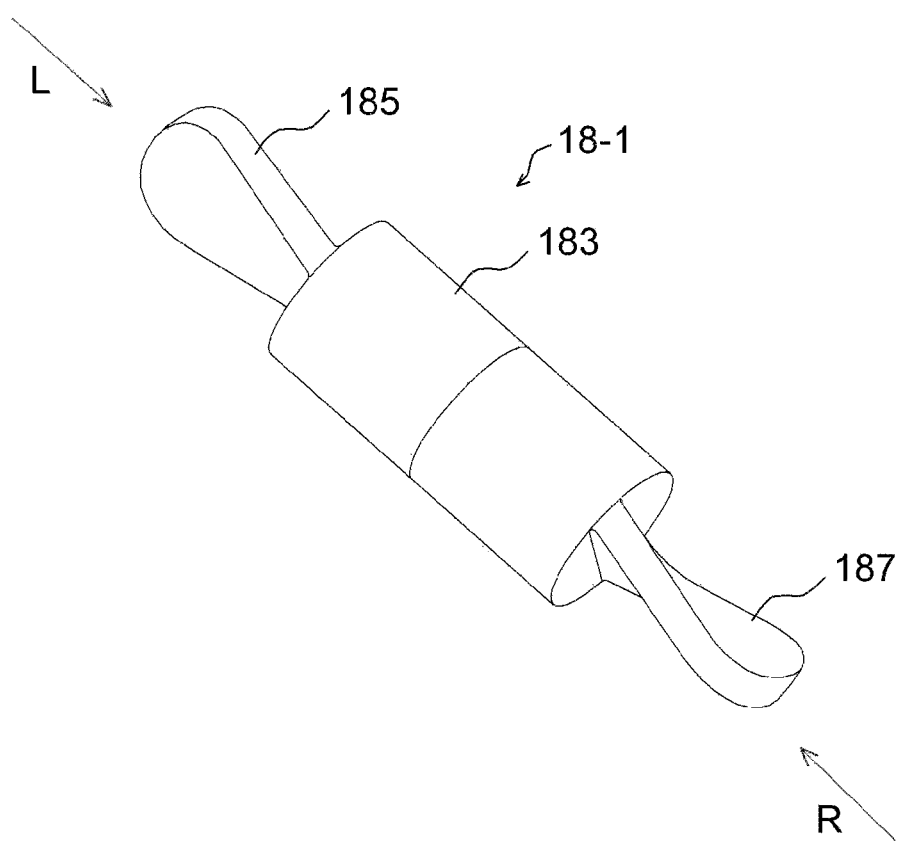
FIGS. 5 to 8 illustrate an example of a stirring rod having a projection part.
Figure 6:
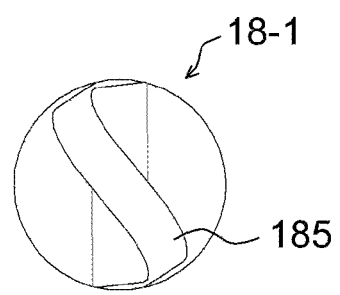
Figure 7:
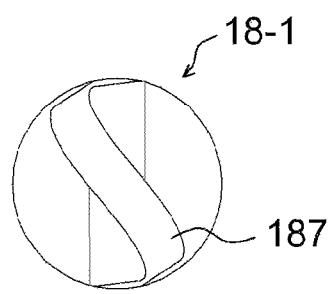
Figure 8:
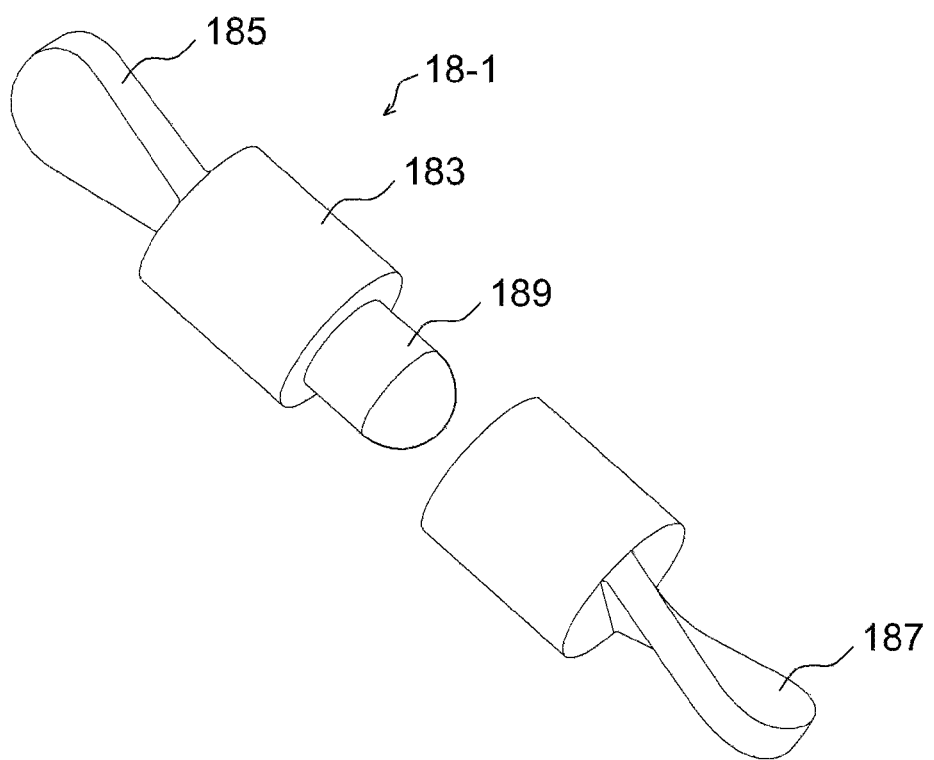
Figure 9:
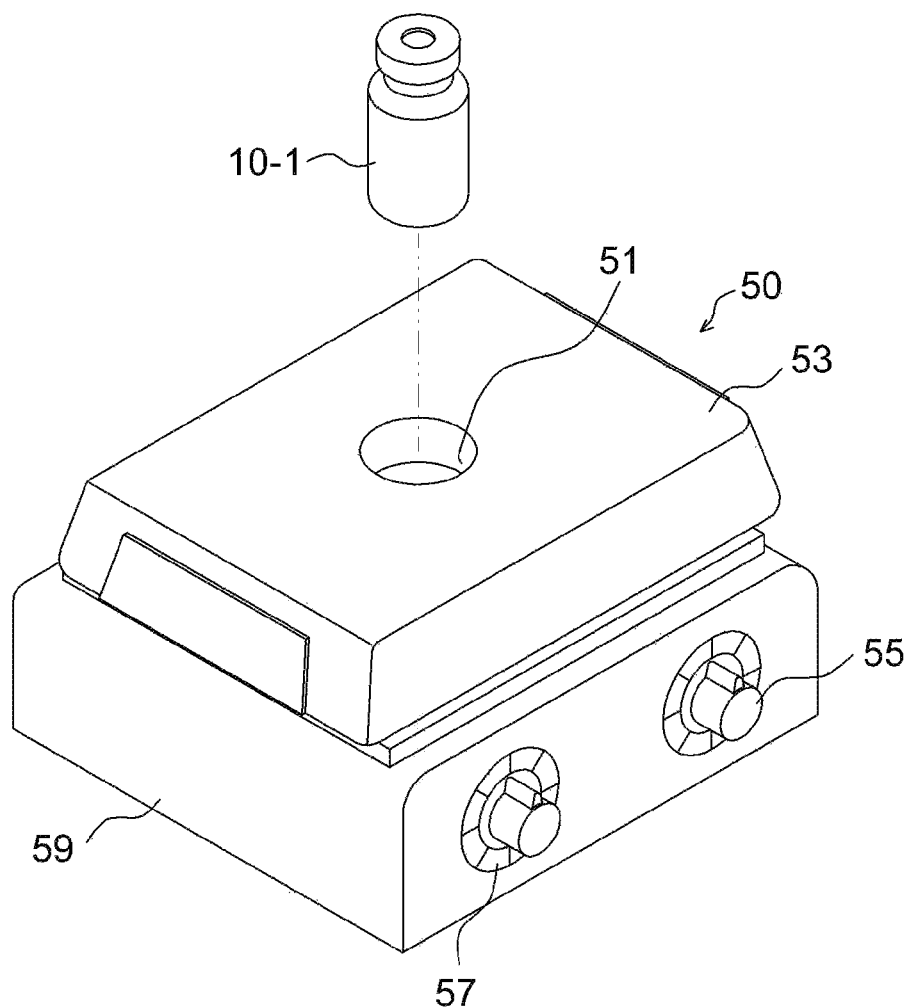
FIG. 9 illustrates an example of a stirrer.
Figure 10:
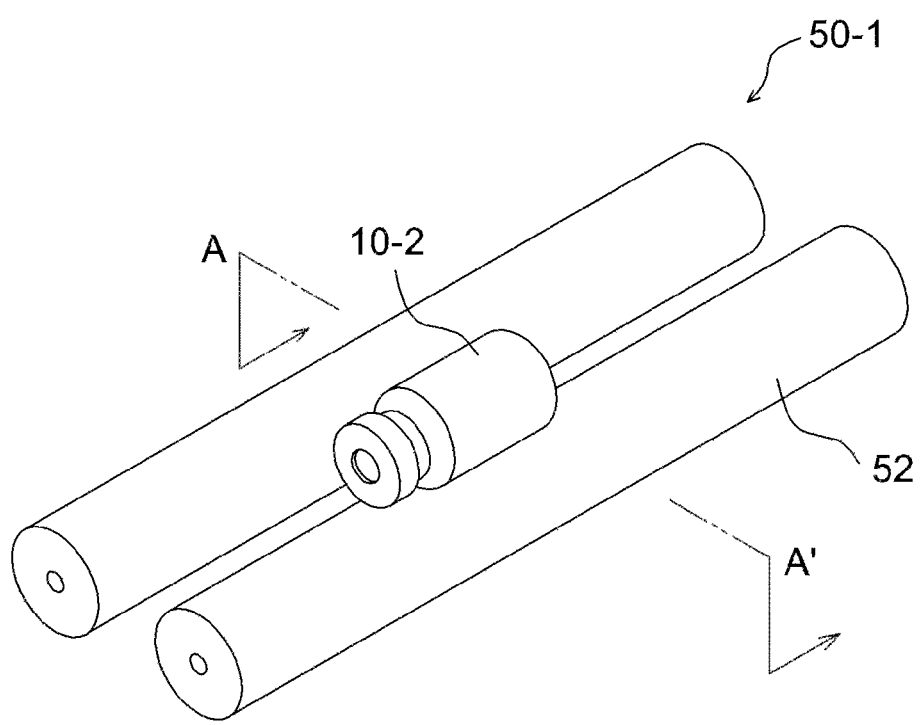
FIGS. 10 and 11 illustrate an additional example of a stirrer.
Figure 11:
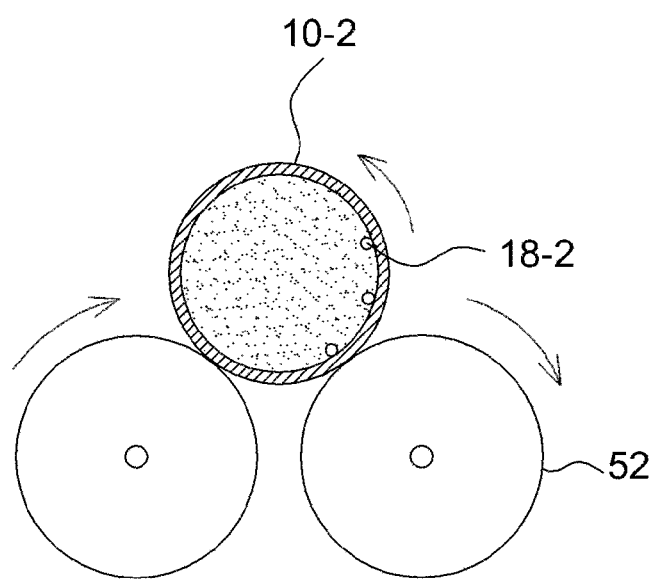
Figure 12:
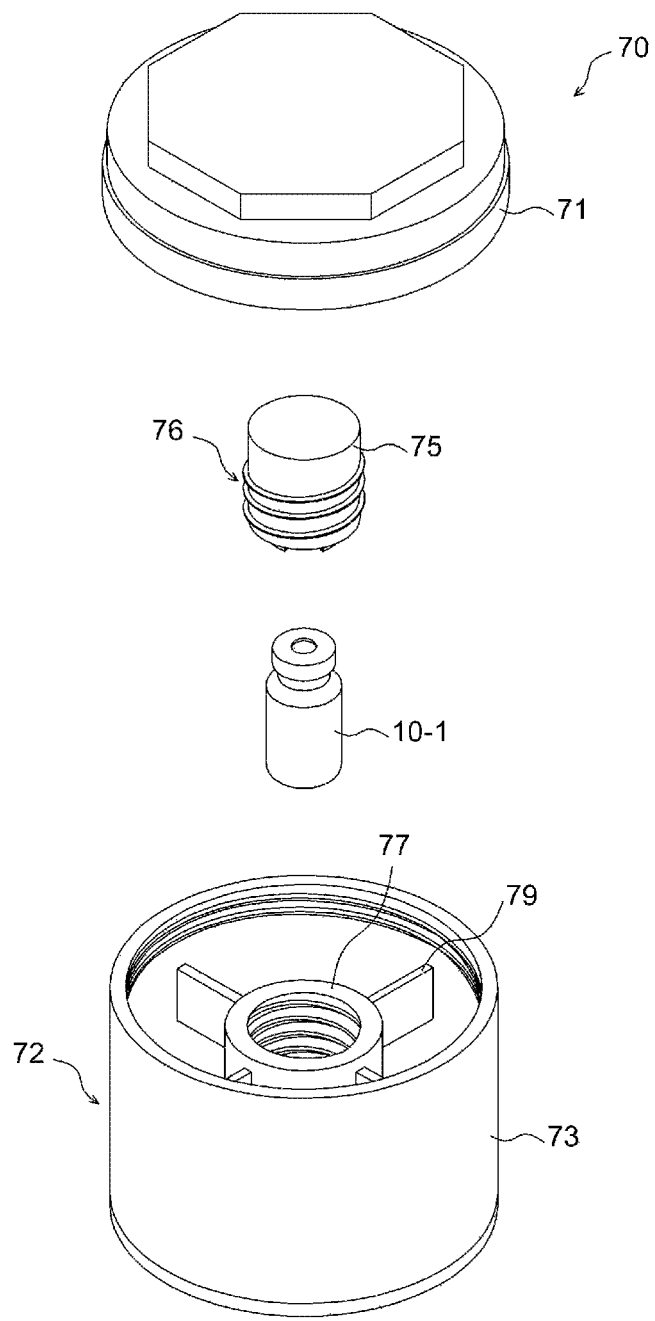
FIGS. 12 to 15 illustrate an example of a temperature control chamber.
Figure 13:
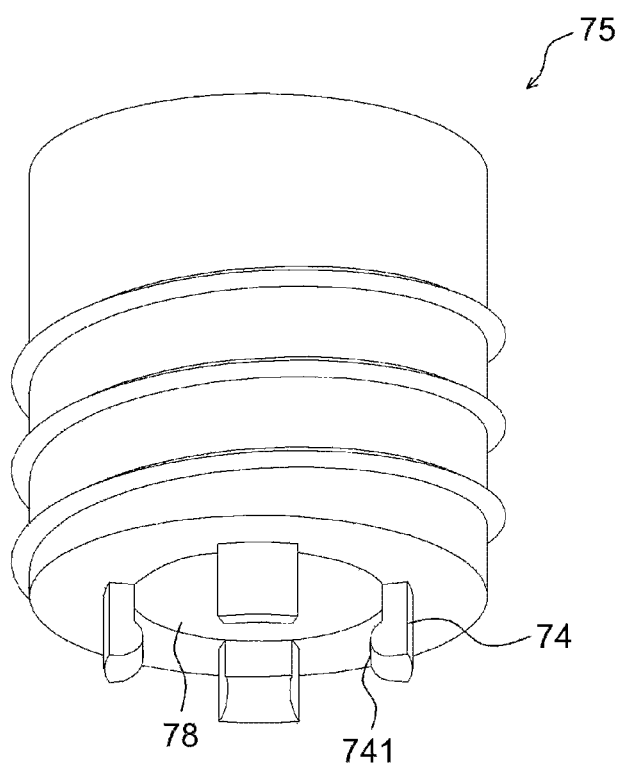
Figure 14:
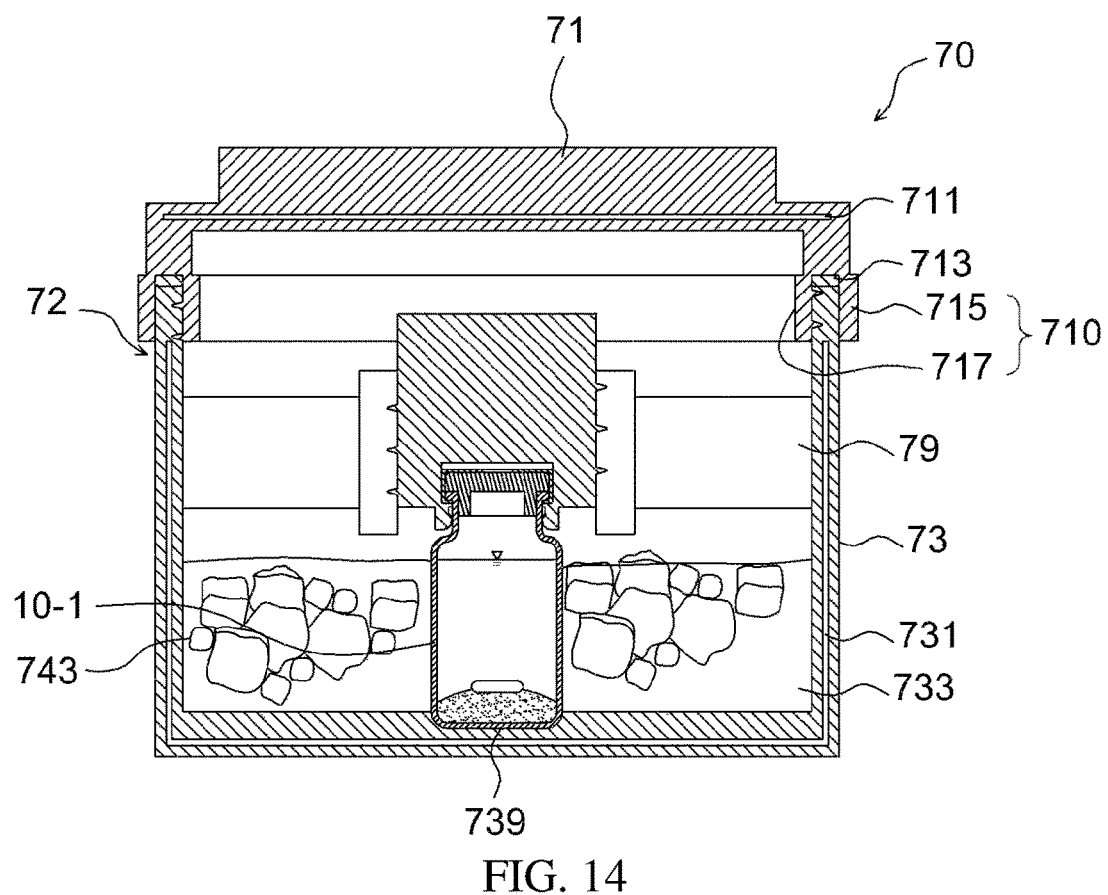
Figure 15:
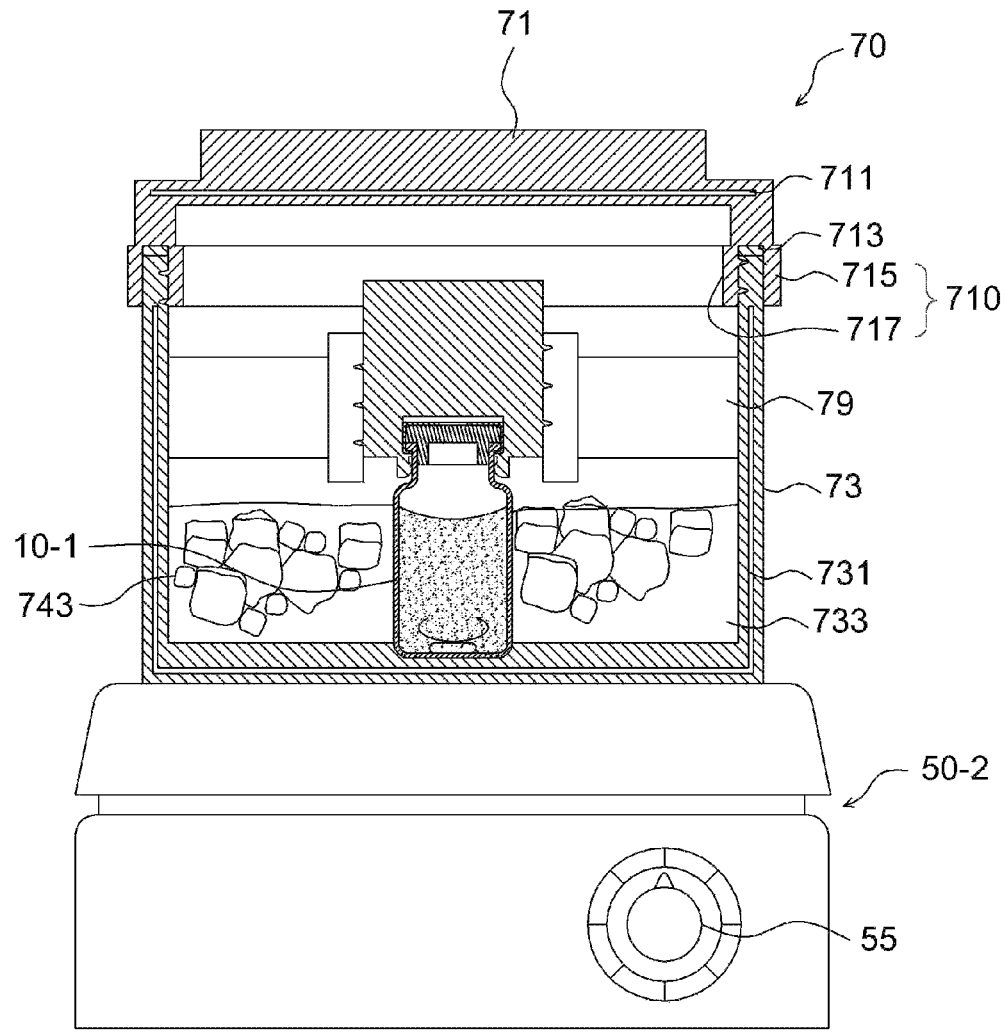
Figure 16:
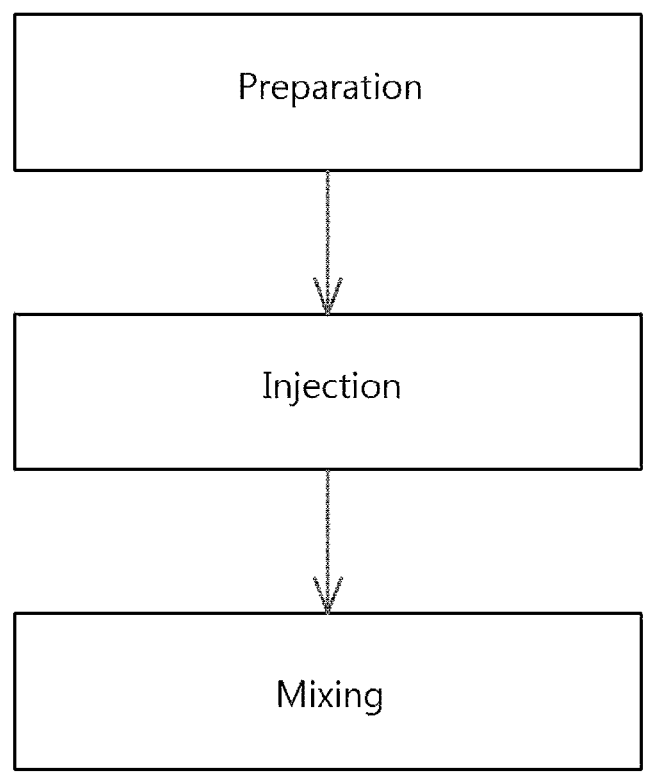
FIG. 16 illustrates a process of preparing a drug delivery system according to an embodiment of the present invention.

FIG. 1 illustrates a drug delivery kit according to an embodiment of the present invention, FIG. 2 is a cross-sectional view illustrating an apparatus for preparing a drug delivery system according to an embodiment of the present invention, FIG. 3 is a perspective view illustrating the drug injection part and the body of the apparatus of FIG. 2, FIG. 4 is a cross-sectional view illustrating an apparatus for preparing a drug delivery system according to a modification of the embodiment of the present invention, FIG. 5 is a perspective view illustrating a stirring rod having a projection part, FIG. 6 is a side view of the stirring rod of FIG. 5 when viewed from the direction of an arrow L, FIG. 7 is a side view of the stirring rod of FIG. 5 when viewed from the direction of an arrow R, FIG. 8 is a partial exploded view of the stirring rod of FIG. 5, FIG. 9 illustrates a stirrer, FIG. 10 illustrates a direct-indirect stirrer, FIG. 11 is a cross-sectional view taken along the line AA' of FIG. 10, FIG. 12 is an exploded view of a temperature control chamber, FIG. 13 illustrates the first subunit of FIG. 12, FIG. 14 is a cross-sectional view of the temperature control chamber of FIG. 12, which is coupled, FIG. 15 illustrates the temperature control chamber of FIG. 14, in the state of currently being used, and FIG. 16 illustrates a process of preparing a drug delivery system according to an embodiment of the present invention.

As illustrated in FIG. 1, the drug delivery kit 1 includes an apparatus 10 for preparing a drug delivery system and a syringe 30. The apparatus 10 for preparing a drug delivery system and the syringe 30 may be packaged in a packaging case 20, and the packaging case 20 may include a cover 22 so as to maintain a more stable state thereof.

Also, one side of the packaging case 20 is provided with an apparatus holding recess 21, a syringe body holding recess 23, and a syringe needle holding recess 25, which receive the apparatus 10 for preparing a drug delivery system, the syringe body 33 and the syringe needle 35, respectively, whereby they may be positioned in place and the packaged state thereof may be easily maintained.

The above apparatus 10 may be an apparatus for preparing a drug delivery system according to an embodiment of the present invention. As illustrated in FIGS. 1 to 3, the apparatus for preparing a drug delivery system according to the embodiment of the present invention includes a drug carrier 17 therein under the airtight condition, and a mixing space 19 may be formed therein. The open side of the apparatus body 11 is closed by means of a drug injection part 13 comprising a sealing stopper such as a rubber stopper, whereby the apparatus may be kept airtight. Also, the open side of the apparatus body is provided with a protrusion 12 that protrudes outwards, and the airtight state of the apparatus may be more stably maintained using a cap 15 that wraps both the protrusion 12 and the drug injection part 13. The cap 15 may be made of an aluminum, etc. The cap 15 is configured such that an opening 16 is formed in the top thereof, thus exposing one side of the drug injection part 13 to the outside. The drug injection part 13 may be provided in any form, including the form of a removable cover, as well as the illustrated rubber stopper, and may be provided in the form of a sealing stopper such as a rubber stopper, as illustrated in the drawing, whereby the syringe needle may be easily placed in or withdrawn from the apparatus, and simultaneously the inside of the apparatus may be kept airtight even when the syringe needle is placed in or withdrawn from the apparatus, ultimately preventing problems in which the drug carrier is undesirably discharged outside during the drug mixing process.

The mixing space 19 is positioned between the drug injection part 13 and the drug carrier 17, whereby the drug injected through the drug injection part 13 may be effectively mixed with the drug carrier.

The drug carrier is provided in the form of a gel phase or a solid phase, and may be a material that is able to form a drug delivery system with the drug. The drug may be injected into the apparatus for preparing a drug delivery system, together with or separately from a solvent. The solvent may be a solvent for forming a drug delivery system. The solvent for forming a drug delivery system may be injected into the apparatus, together with or separately from the drug. As such, the drug may be in the state of being dissolved or suspended in the solvent. This solvent may be a solvent for dissolving or suspending a drug carrier, especially a drug carrier in a solid phase. A solvent that may dissolve or suspend both the drug and the drug carrier is used, thus facilitating the formation of the drug delivery system.

At least one solvent, selected from among a solvent for dissolving or suspending a drug carrier and a solvent for dissolving or suspending a drug, is injected from the outside into the apparatus for preparing a drug delivery system, whereby the drug carrier and/or the drug may be dissolved or suspended, and may thus be more easily mixed.

The solvent, which is a material for dissolving and/or suspending the drug and/or the drug carrier, may be exemplified by water. The water may be physiological saline. Alternatively, the water may be deionized water.

The drug carrier may include, for example, a gel-forming polymer. The gel-forming polymer is added with the drug and, optionally, with the solvent as well, and is then mixed therewith, yielding a gel.

The gel-forming polymer may include, for example, at least one selected from among an N-isopropyl acrylamide polymer, ethyl hydroxyethyl cellulose, poly(ethylene oxide-propylene oxide-ethylene oxide), poloxamer, Pluronics® polymers, poly(ethylene glycol)/poly(D,L-lactic acid-co-glycolic acid) block copolymers, polysaccharides, alginate, polyphosphazene, polyacrylate, Tetronics™ polymers, and polyethylene oxide-polypropylene glycol block copolymers. Poly(ethylene oxide-propylene oxide-ethylene oxide) is a block copolymer, and may be poly(ethylene oxide-b-propylene oxide-b-ethylene oxide). Examples of the poly(ethylene oxide-propylene oxide-ethylene oxide) may include those which are prepared or commercially available (Pluronic F127, i.e. poloxamer 407).

Also, the drug carrier may further include a gel-forming assistant for aiding the formation of the polymer gel. The gel-forming assistant functions to aid the physical crosslinking of the gel-forming polymer, and may be exemplified by a hyaluronic acid salt. The hyaluronic acid salt may include sodium hyaluronate, etc.

Specifically, the drug carrier may include the gel-forming polymer and the gel-forming assistant, and such a drug carrier may be a powdery solid mixture. Preferably, the drug carrier is a solid drug carrier, for example, a mixture of poly(ethylene oxide-propylene oxide-ethylene oxide) and sodium hyaluronate, which are a powdery solid.

As such, the gel may be a temperature-sensitive hydrogel. The temperature-sensitive hydrogel may be a temperature-responsive hydrogel, which is a liquid at room temperature and is a solid or gel at body temperature. For example, the temperature-sensitive hydrogel-forming polymer and the temperature-sensitive hydrogel-forming assistant, which are a solid, are dissolved or suspended in a solvent, and may thus be converted into a liquid at room temperature and into a solid or gel at body temperature. The temperature-sensitive hydrogel may be mixed with the drug to thus form the drug delivery system.

Here, the liquid exhibits a viscosity of about 10 Pas, and the gel exhibits a viscosity of about 300 Pas.

The drug carrier, especially a solid drug carrier, may be a lyophilized material. The lyophilized material may be a drug carrier resulting from a lyophilization process. The solid drug carrier may be a lyophilized material obtained by typically lyophilizing the gel-forming polymer alone or in combination with the gel-forming assistant using a typical lyophilization process. For example, the drug carrier may be a lyophilized material obtained by adding 20 wt % of poly(ethylene oxide-propylene oxide-ethylene oxide) and 0.6 wt % of sodium hyaluronate with the balance of water, stirring them to give a stirred product, which is then frozen in the temperature range from −40° C. to −30° C., followed by sublimating water in a vacuum. The drug carrier, which is a lyophilized material, may be more easily dissolved in the solvent.

The drug delivery system is preferably a liquid at room temperature (20±5° C.) and a gel or solid at body temperature (37±5° C.). Briefly, the drug delivery system may contain a temperature-sensitive hydrogel. For example, the drug delivery system may be made to have a liquid phase at room temperature and a gel phase or a solid phase at body temperature by dissolving or suspending, in the solvent, the drug and the drug carrier for forming a temperature-sensitive hydrogel. Since the temperature-sensitive hydrogel is a liquid at room temperature and a gel or solid at body temperature, the liquid drug delivery system prepared using the apparatus for preparing a drug delivery system at room temperature may be easily taken out using a syringe, and is thus readily handled. After administration, such a liquid drug delivery system becomes a gel, whereby the retention time of the drug in the region of administration may be increased.

Also, the drug delivery system may have a solid phase, in addition to the gel phase. As such, the temperature-sensitive hydrogel is not limited to the gel phase, but is used to have a meaning including a solid phase. The temperature-sensitive hydrogel may have a gel phase or a solid phase at body temperature. The phase transition from a liquid to a gel may be a physical change. Thus, based on a physical change, the drug may be released in a desired pattern at a desired portion, without affecting the activity of the drug contained in the drug delivery system.

The above description is applied to the case where the drug carrier mainly has a solid phase, but a drug carrier in a gel phase may be contained in the apparatus for preparing a drug delivery system. As such, the gel may be exemplified by a temperature-sensitive hydrogel. The apparatus for preparing a drug delivery system is filled with the gel-forming polymer, which has a gel phase with the addition of a solvent, and is then sealed hermetically, whereby the drug carrier in a gel phase may be incorporated in the apparatus for preparing a drug delivery system. For example, as illustrated in FIG. 3, the apparatus body 11 is filled with the drug carrier in a gel phase, and is then closed with the drug injection part 13, constituted of a sealing stopper, so that the drug carrier in a gel phase may be incorporated in the apparatus for preparing a drug delivery system. As such, the drug injection part may be capped using a capping machine. When the drug carrier has a gel phase in this way, the drug is injected and mixed, thereby easily forming the drug delivery system.

The drug may be injected into the apparatus for preparing a drug delivery system, together with or separately from the solvent. The drug may be in the state of being dissolved or suspended in the solvent. When the drug is injected together with the solvent, the drug delivery system may be prepared, without the additional use of the solvent. The solvent may be added as necessary.

The drug, which is dissolved or suspended in the solvent, may be at least a portion of the drug, and is preferably all of the drug.

Also, at least a portion of the drug may be provided in the form of being incorporated in a microsphere. Such a microsphere may be in the state of being suspended in a solvent, and at least a portion of the drug may be contained in the microsphere, and the remainder of the drug may be dissolved or suspended in the solvent in which the microsphere is suspended. When a portion of the drug is contained in the microsphere in this way, the drug delivery system may include the microsphere containing the drug, and the drug may be released in vivo by an independent release pattern of only the microsphere, in addition to the drug release pattern of the drug delivery system formed by mixing the drug and the drug carrier. Accordingly, the release of the drug may be more effectively controlled. The microsphere has a small size and may thus pass through the syringe needle. For example, the microsphere may have an average particle diameter of 10 mm.

The microsphere containing the drug may be prepared through any process known in the art.

For example, the microsphere may be prepared from a biodegradable polymer selected from the group consisting of polylactic acid, polyglycolic acid, polyhydroxybutyric acid, poly-γ-caprolactone, poly-δ-valerolactone, lactic acid-glycolic acid copolymer, poly(alpha-hydroxy acid), poly(lactone), poly(amino acid), poly(ortho-ester), poly(ortho-carbonate), poly(phosphoester), poly(DL-lactic acid), poly(L-lactic acid), poly(lactone), poly(delta-valerolactone), poly(gamma-butyrolactone), poly(1,5-dioxepan-2-one), poly(trimethylene carbonate), poly lactic-co-glycolic acid, poly(valerolactone), poly(ε-caprolactone), poly[bis(p-carboxyphenoxy)propane-co-sebacic acid], poly(fatty acid dimer-co-sebacic acid), aryloxy phosphazene polymers, blends and copolymers of these polymers.

Any drug may be mixed with the drug carrier and used without limitation, so long as its principal function exhibits bioactivity, and may include, for example, at least one selected from the group consisting of an anesthetic agent, an analgesic agent, an anti-angiogenic agent, a vascular activator, an anticoagulant, a cytotoxic agent, a neurotransmitter, an anti-cancer agent, an antibiotic agent, an antiviral agent, an anorectic agent, an anti-arthritis agent, an anti-asthma agent, an anticonvulsant, an antidepressant, an antihistamine, an anti-inflammatory agent, an antiemetic agent, an antimigraine agent, an anti-tumor agent, an anti-itching agent, an antipsychotic agent, an antipyretic agent, an antispasmodic agent, a cardiovascular formulation (including a calcium channel blocker, a beta-blocker, a beta-agonist, or an antiarrhythmic agent), an antihypertensive agent, a chemotherapeutic agent, a diuretic, a vasodilator, a central nervous system stimulant, a cough cold preparation, a decongestant, a diagnostic agent, a hormone, a bone formation stimulant, a bone resorption inhibitor, an immunomodulator, an immunosuppressive agent, a muscle relaxant, a mental agonist, a psychostimulant, a sedative agent, a tranquilizer, a protein, a peptide (including those spontaneously generated, chemically synthesized or recombined), a nucleic acid molecule (including a polymer of two or more nucleic acids, ribonucleotides or deoxyribonucleotides including double- and single-stranded molecules and supercoiled or condensed molecules, gene constructs, expression vectors, plasmids, antisense molecules, etc.), an antibody, a lipid, a cell, a tissue, a vaccine, a gene, and a polysaccharide.

The syringe 30 is used to inject the drug into the apparatus for preparing a drug delivery system, and may include, but is not limited to, a syringe body 33 and a syringe needle 35.

One side of the syringe needle 35 is provided with a body connector 351 for removably attaching the syringe needle to the syringe body 33, and one side of the syringe body 33 is provided with a syringe needle connector 331 that is connected to the body connector 351. Disposed in the syringe body 33 is a piston 335, whereby external material may be introduced into the syringe body or internal material may be discharged therefrom. The syringe body 33 and the syringe needle 35 are provided in separated form or in combined form.

By rotating or vibrating the apparatus for preparing a drug delivery system, the drug and the drug carrier may be mixed, and more effective mixing is possible using a stirring element and/or a stirrer, as will be described later.

As illustrated in FIG. 4, the apparatus 10-1 may further include a stirring element 18 therein so as to enable more effective mixing.

Such a stirring element functions to aid the mixing process using external force. When the mixing is facilitated by external force using the stirring element in this way, the weight of the apparatus itself may be reduced, and in particular, the apparatus for preparing a drug delivery system may be easily used on site.

For example, the stirring element may include at least one selected from among a stirring magnet, a stirring rod, a stirring plate, and a stirring ball. When the stirring magnet is rotated by an external magnetic force, more simple and effective mixing is possible. Furthermore, the stirring element, such as a stirring rod, a stirring plate, or a stirring ball, is included in the apparatus, which is then rotated or vibrated using external force, thereby enabling more effective mixing using the stirring element.

The stirring element is provided in the form of a stirring rod, and may include a stirring magnet therein. For example, the stirring element 18 illustrated in FIG. 4 is a stirring rod that is provided in the form of a rod and includes a stirring magnet therein. Such a stirring element may be commercially available.

Alternatively, as illustrated in FIGS. 5 to 8, the stirring element 18-1 may be configured such that a stirring magnet 189 is provided in a stirring rod body 183, and one or more sides thereof may include projection parts 185, 187. The projection parts 185, 187 are formed in the long-axis direction of the stirring rod, thus enabling more effective stirring. More preferably, the surface of each projection part may be formed to be curvilinear, thereby enabling more efficient rotation. As illustrated in FIGS. 5 to 7, the projection parts may have a screw shape. Also, as illustrated in FIG. 8, the stirring rod body 183 may be divided into two sections.

Also, the kit according to the present invention may further include a stirrer.

The drug carrier and the drug may be easily mixed by means of the stirrer, either alone or in combination with the stirring element.

The stirrer is not limited so long as it is used to mix the drug and the drug carrier, and may include, for example, at least one selected from among a direct stirrer, an indirect stirrer, and a direct-indirect stirrer.

The direct stirrer is used to directly mix the drug carrier and the drug, and examples thereof may include a magnetic stirrer, an ultrasonic stirrer, etc.

The indirect stirrer is used to indirectly mix the drug carrier and the drug through the motion of the apparatus, and examples thereof may include a revolution-rotation stirrer, a vibration stirrer, a rotary stirrer, a vortex mixer, a rotator, a microplate mixer, a shaker, and a roller stirrer.

The direct-indirect stirrer is used to indirectly mix the drug carrier and the drug while directly mixing them, and may be exemplified by a ball mill stirrer.

The stirrer is commercially available, and the magnetic stirrer is described with reference to FIG. 9.

The stirrer 50 is configured such that a magnet for rotating the stirring magnet is positioned inside the stirrer body 59 and a speed control part 55 for controlling the rotational speed is positioned outside the stirrer body, thus rotating the stirring magnet (not shown) provided in the apparatus 10-1 for preparing a drug delivery system to thereby mix the drug carrier and the drug.

As such, the stirrer includes a support 53 for supporting the apparatus for preparing a drug delivery system, and the support includes a holding recess 51 that receives at least a portion of the apparatus 10-1 for preparing a drug delivery system, thus more stably supporting the apparatus 10-1. Such a holding recess may be formed by recessing the support of a commercially available magnetic stirrer. Such a recess may be directly formed in the support, or may be formed by mounting a plate, having therein a through hole, on the support.

The ball mill stirrer, which is an example of the direct-indirect stirrer, is described with reference to FIGS. 10 and 11.

As illustrated in the drawings, a stirring element 18-2, such as a stirring ball, is provided inside the apparatus 10-2 for preparing a drug delivery system, and a stirrer 50-1, such as a roller stirrer, is applied outside the apparatus, whereby direct mixing using the stirring ball and indirect mixing using the roller 52 are simultaneously carried out, thus effectively mixing the drug and the drug carrier.

The stirrer 50 may include a temperature controller 57. The temperature controller 57 is used to control the temperature so as to meet the requirement for preparing the drug delivery system. The temperature may be decreased using a cooling medium or increased using a heating medium or a heat line. The heating medium (or the heat line) and the cooling medium may be brought into contact with the support, and the heating medium and the cooling medium may be controlled by the temperature controller. The heating medium is used to dissipate heat, and may include heating medium oil and warm water. The cooling medium is used to absorb heat, and may include a synthetic compound, for use in refrigerators, or ice water. A commercially available stirrer with a temperature controller may be used.

Also, the kit according to the present invention may further include a temperature control chamber.

The temperature control chamber functions as the temperature controller of the stirrer. Thereby, even when a stirrer having no temperature controller is applied to the kit, the temperature may be easily adjusted. On-site use of the temperature control chamber makes it easy to adjust the temperature conditions necessary for the preparation of the drug delivery system.

As illustrated in FIGS. 12 to 14, the temperature control chamber 70 may include a casing 72, an apparatus fixer 76, and a temperature control medium holding recess 733.

The casing 72 includes a casing body 73 and a lid 71, and may accommodate therein the apparatus 10-1 for preparing a drug delivery system. The casing body 73 and the lid 71 may be removably attached to each other through screw coupling. The casing 72 includes heat insulation layers 711, 731 on at least portions thereof, thereby more easily responding to changes in the temperature.

A packing 713 made of rubber may be disposed between the lid 71 and the casing body 73, and one end of the lid 71 may be provided with a coupling part 710 comprising an outer coupling part 715 and an inner coupling part 717, which face each other, and between respective ends of which the casing body 73 is interposed. The coupling part 710 is a portion at which the lid 71 and the casing body 73 are coupled to each other, and the outer coupling part 715 contacts the outer surface of the casing body 73 and the inner coupling part 717 contacts the inner surface of the casing body 73. At these contact portions, the lid 71 and the casing body 73 may be coupled to each other through screw coupling.

The apparatus fixer 76 is used to fix the apparatus 10-1 for preparing a drug delivery system, and may include a first subunit 75, which directly contacts the apparatus 10-1 for preparing a drug delivery system, and a second subunit 77 for fixedly connecting the first subunit to the casing.

One side of the first subunit 75 is provided with fixing ends 74, which protrude in the direction toward the apparatus for preparing a drug delivery system to fix the apparatus, and the remaining side of the first subunit may be removably fixed to one side of the second subunit. Each of the fixing ends 74 may include a projection 741 that projects inwards. This removable fixing may be realized through, for example, screw coupling.

To this end, the inner side of the second subunit 77 is connected to the outer side of the first subunit 75, and the outer side of the second subunit 77 may be connected to the inner side of the casing 72 by means of a connector 79. Furthermore, one side of the first subunit 75 may include an insertion part 78, into which the top of the apparatus for preparing a drug delivery system is inserted, at a position enclosed by a plurality of fixing ends. The insertion part 78 and the fixing ends 74 enable the apparatus for preparing a drug delivery system to be maintained more stably. Also, the inner side of the casing may include an insertion depression 739, into which the bottom of the apparatus 10-1 for preparing a drug delivery system is fixedly fitted, thus more firmly fixing the apparatus for preparing a drug delivery system. Thereby, more stable mixing becomes possible by virtue of the insertion part, fixing ends, and insertion depression.

Also, the temperature control medium holding recess 733 includes a temperature control medium received therein, and the temperature control medium may be a heating medium for dissipating heat or a cooling medium for absorbing heat. The temperature control medium 743 is exemplified by ice water in the drawing, but the present invention is not limited thereto.

As illustrated in FIG. 15, the apparatus 10-1 for preparing a drug delivery system is placed into the temperature control chamber 70, in order to prepare a drug delivery system. When the temperature control chamber is used in this way, the temperature may be adjusted to a level appropriate for preparation of the drug delivery system, even without the additional use of a temperature control means. Thus, the stirrer 50-2, for example, a commercially available magnetic stirrer having a stirring speed control part 55, may be used, thus facilitating the preparation of the drug delivery system.

A user's guide that describes the use of the apparatus is incorporated in the kit according to the present invention, so that the kit or apparatus of the present invention may be more easily used by a user.

The user's guide is provided in the form of an additional paper sheet and is thus incorporated in the packaging case, or may be printed on the packaging case itself and may thus be incorporated in the kit of the present invention.

With reference to FIG. 16, the method of preparing a drug delivery system according to an embodiment of the present invention is specified below.

As illustrated in the drawing, the method of preparing the drug delivery system according to the embodiment of the present invention includes (A) preparation, (B) injection, and (C) mixing.

The preparation (A) is a step of providing an apparatus for preparing a drug delivery system, which includes therein a drug carrier in a gel phase or a solid phase under the airtight condition, and has a mixing space configured such that a drug for forming a drug delivery system with the drug carrier is injected from the outside and is mixed with the drug carrier. Here, the apparatus for preparing a drug delivery system may fall under the same scope as the apparatus of the present invention. As mentioned above, the apparatus of the present invention is applied, whereby the drug delivery system may be more easily prepared on site.

The injection (B) is a step of injecting the drug into the apparatus for preparing a drug delivery system, and may be performed using a syringe. The syringe may fall under the same scope as the syringe included in the drug delivery kit of the present invention.

The drug may be injected into the apparatus, together with or separately from a solvent. The solvent may be a solvent for forming the drug delivery system. The solvent for forming the drug delivery system may be injected into the apparatus, together with or separately from the drug. When the drug is injected together with the solvent, the drug may be in the state of being dissolved or suspended in the solvent. Such a solvent may be a solvent for dissolving or suspending a drug carrier, especially a solid drug carrier. The drug and the drug carrier are dissolved or suspended using the same solvent, whereby the drug delivery system may be formed more easily.

The mixing (C) is a step of mixing the drug and the drug carrier in the mixing space to form the drug delivery system. The mixing may be performed using a stirrer, which may fall under the same scope as the stirrer that may be included in the kit of the present invention.

The mixing (C) may be performed using a stirring element, which may fall under the same scope as the stirring element that may be included in the apparatus of the present invention.

The mixing (C) may be performed under the condition that the apparatus, into which the drug and the drug carrier are injected, is placed into the temperature control chamber. The temperature control chamber may fall under the same scope as the temperature control chamber included in the drug delivery kit of the present invention.

Also, the mixing (C) may be performed under the condition that the apparatus is provided with the stirring element, which may fall under the same scope as the stirring element that may be included in the apparatus of the present invention.

In the preparation method according to a modified embodiment of the present invention, at least one solvent selected from among a solvent for dissolving or suspending a drug carrier and a solvent for dissolving or suspending a drug may be injected from the outside into the apparatus for preparing a drug delivery system, whereby the drug carrier and/or the drug may be dissolved or suspended and thus may be more easily mixed, thus yielding a drug delivery system. For example, the preparation method according to a modified embodiment of the present invention may further include injecting at least one solvent, selected from among a solvent for dissolving or suspending a drug carrier and a solvent for dissolving or suspending a drug, from the outside into the apparatus for preparing a drug delivery system. This injection step may be implemented between the step (A) and the step (B), simultaneously with the step (B), between the step (B) and the step (C), or simultaneously with the step (C).

The solvent is a material for dissolving and/or suspending the drug and/or the drug carrier, and may include, for example, water. The water may be physiological saline. Alternatively, the water may be deionized water.

The drug or the drug carrier may fall under the same scope as the drug or the drug carrier, which is injected into the apparatus of the present invention.

A better understanding of the present invention may be obtained through the following Embodiment A.

Embodiment A

An apparatus for preparing a drug delivery system as illustrated in FIG. 4 was provided. The drug carrier in the apparatus was a mixture comprising poly(ethylene oxide-propylene oxide-ethylene oxide) (Pluronic F127) and sodium hyaluronate, which are a powdery solid. The stirring magnet was a commercially available stirring magnet coated with Teflon. As such, based on the amount of added Bupivacaine HCl solution, the amount of poly(ethylene oxide-propylene oxide-ethylene oxide) was 20 w/v %, and the amount of sodium hyaluronate was 0.6 w/v %. The Bupivacaine HCl solution (in an amount of the balance) as an anesthetic agent was injected into the apparatus using a syringe with an 18-gauge needle. The Bupivacaine HCl solution was a typically useful 0.5% (100 mg/20 ml) colorless clear injection solution, obtained by dissolving a 1.3% Bupivacaine HCl powder in physiological saline.

Also, a temperature control chamber as illustrated in FIG. 12 was provided.

The top of the apparatus for preparing a drug delivery system was fixed to fixing ends of the first subunit as illustrated in FIG. 13, and the first subunit was screw-coupled to the second subunit, thus providing the apparatus illustrated in FIG. 14. As such, the temperature control medium holding recess was filled with physiological saline containing ice water and covered with a lid so that the temperature inside the temperature control chamber was 4° C. to 8° C.

As illustrated in FIG. 15, the mixing was performed for 2 hr using a magnetic stirrer, yielding a drug delivery system. The drug delivery system obtained thus may be transferred into a syringe body using an 18-gauge syringe needle, and may be used on medical sites through injection into or spraying onto the target region.

The drug delivery system has low viscosity at room temperature (e.g. a viscosity of 10 Pas at 20° C.), thus facilitating injection of the drug using a syringe, and the viscosity thereof in vivo may relatively increase (e.g. a viscosity of 300 Pas at 37° C.), thereby slowly releasing the drug. In in-vitro testing, the drug was released in an amount of 40 to 50 wt % on the first day, and was slowly released over a long period of time (10 days or longer). Also, in in-vivo testing, the drug was released in an amount of about 50 wt % on the first day, and the hydrogel became loose after 3 to 5 days, whereby the drug and the hydrogel were absorbed in vivo and disappeared.

As described hereinbefore, the common descriptions are omitted in order to avoid undue redundancy leading to the complexity of this specification. Further, although the preferred embodiments of the present invention regarding the drug delivery kit and the apparatus and method for preparing a drug delivery system have been disclosed for illustrative purposes, those skilled in the art will appreciate that various modifications, additions and substitutions are possible, without departing from the scope and spirit of the present invention as disclosed in the accompanying claims.

INDUSTRIAL APPLICABILITY

The present invention facilitates on-site preparation of a drug delivery system to thus deliver a drug in vivo, and is thus industrially applicable.

The invention claimed is:

1. A drug delivery kit, comprising:
an apparatus for preparing a drug delivery system, the apparatus including a drug carrier in a gel phase or a solid phase under an airtight condition, and a mixing space configured such that a drug is injected from outside and is mixed with the drug carrier to form a drug containing gel; and a syringe for injecting the drug into the apparatus, wherein the drug carrier comprises a gel-forming polymer.

2. The drug delivery kit of claim 1, wherein the drug is dissolved or suspended in a solvent, or at least a portion of the drug is contained in a microsphere.

3. The drug delivery kit of claim 1, wherein the drug carrier further comprises a gel-forming assistant for aiding formation of a polymer gel.

4. The drug delivery kit of claim 1, wherein the drug delivery system is a liquid at room temperature and is a gel or solid at body temperature.

5. The drug delivery kit of claim 1, wherein the drug carrier in the solid phase is a mixture comprising poly (ethylene oxide-propylene oxide-ethylene oxide) and sodium hyaluronate, which are a solid.

6. The drug delivery kit of claim 1, wherein the apparatus includes a drug injection part at one side thereof so that a syringe needle is placed in or withdrawn from the apparatus and so that an inside of the apparatus is kept airtight when the syringe needle is placed in or withdrawn from the apparatus.

7. The drug delivery kit of claim 1, wherein the apparatus further includes a stirring element therein.

8. The drug delivery kit of claim 7, wherein the stirring element includes at least one selected from among a stirring magnet, a stirring rod, a stirring plate, and a stirring ball.

9. The drug delivery kit of claim 8, wherein the stirring rod is provided in rod form, and includes a stirring magnet therein.

10. The drug delivery kit of claim 8, wherein at least one side of the stirring rod includes a projection part.

11. The drug delivery kit of claim 1, further comprising a temperature control chamber.

12. The drug delivery kit of claim 11, wherein the temperature control chamber comprises a casing, an apparatus fixer for fixing the apparatus in the casing, and a temperature control medium holding recess for receiving a temperature control medium in the casing.

13. The drug delivery kit of claim 12, wherein the apparatus fixer comprises a first subunit that directly contacts the apparatus and a second subunit for fixedly connecting the first subunit to the casing.

14. The drug delivery kit of claim 13, wherein one side of the first subunit includes a fixing end formed to protrude in a direction toward the apparatus so as to fix the apparatus, and a remaining side of the first subunit is removably fixed to one side of the second subunit.

15. The drug delivery kit of claim 1, further comprising a stirrer for mixing the drug carrier and the drug, which are maintained in the apparatus for preparing the drug delivery system.

16. The drug delivery kit of claim 15, wherein the stirrer comprises at least one selected from among a direct stirrer for directly mixing the drug carrier and the drug, an indirect stirrer for indirectly mixing the drug carrier and the drug through motion of the apparatus, and a direct-indirect stirrer for indirectly mixing the drug carrier and the drug while directly mixing the drug carrier and the drug.

17. The drug delivery kit of claim 1, wherein the drug carrier in the solid phase is a lyophilized material.

18. An apparatus for preparing a drug delivery system, comprising:

a drug carrier in a gel phase or a solid phase under an airtight condition; and a mixing space configured such that a drug is injected from outside and is mixed with the drug carrier to form a drug containing gel, wherein the drug carrier comprises a gel-forming polymer.

19. The apparatus of claim 18, wherein the drug carrier in the solid phase is a lyophilized material.

20. The apparatus of claim 18, wherein the apparatus is placed into a temperature control chamber.

21. A method of preparing a drug delivery system, comprising:

providing an apparatus for preparing the drug delivery system, the apparatus including a drug carrier in a gel phase or a solid phase under an airtight condition, and a mixing space, wherein the drug carrier comprises a gel-forming polymer;

injecting the drug into the apparatus; and mixing the drug and the drug carrier in the mixing space to form a drug containing gel.

22. The method of claim 21, wherein the injecting is performed using a syringe.

23. The method of claim 21, wherein the mixing is performed under a condition that the apparatus, into which the drug and the drug carrier are injected, is placed into a temperature control chamber.

* * * * *